(12) United States Patent
Marincek et al.

(10) Patent No.: US 7,778,306 B2
(45) Date of Patent: Aug. 17, 2010

(54) LASER SYSTEM

(75) Inventors: Marko Marincek, Ljubljana (SI); Boris Cencic, Ljubljana (SI)

(73) Assignee: Fotona d.d., Ljubljana (SI)

( * ) Notice: Subject to any disclaimer, the term of this patent is extended or adjusted under 35 U.S.C. 154(b) by 198 days.

(21) Appl. No.: 12/107,124

(22) Filed: Apr. 22, 2008

(65) Prior Publication Data

US 2008/0267247 A1    Oct. 30, 2008

(30) Foreign Application Priority Data

Apr. 26, 2007    (EP)    .................................. 07008465

(51) Int. Cl.
*H01S 3/08* (2006.01)
(52) U.S. Cl. .................. 372/103; 372/101; 372/99; 372/98; 372/25; 372/55
(58) Field of Classification Search .................. 372/103, 372/101, 99, 98, 10, 25, 55
See application file for complete search history.

(56) References Cited

U.S. PATENT DOCUMENTS

| 4,941,093 | A | | 7/1990 | Marshall et al. | |
|---|---|---|---|---|---|
| 5,394,411 | A | * | 2/1995 | Milchberg et al. | 372/5 |
| 6,451,010 | B1 | * | 9/2002 | Angeley | 606/17 |
| 7,110,171 | B2 | * | 9/2006 | Dane et al. | 359/347 |
| 2007/0091968 | A1 | * | 4/2007 | Wakabayashi et al. | 372/55 |

FOREIGN PATENT DOCUMENTS

| DE | 3800555 A1 | 7/1989 |
|---|---|---|
| JP | 07184915 A | 7/1995 |
| WO | 01/78633 A2 | 10/2001 |

OTHER PUBLICATIONS

J. Sun and J.P. Longtin; Inert gas beam delivery for ultrafast laser micromachining at ambient pressure; Journal of Applied Physics; vol. 89, No. 12; Jun. 15, 2001; pp. 8219-8224 (see attached EP search report).

* cited by examiner

*Primary Examiner*—Minsun Harvey
*Assistant Examiner*—Kinam Park
(74) *Attorney, Agent, or Firm*—Gudrun E. Huckett

(57) ABSTRACT

The invention relates to laser system with a laser source and an articulated arm. The articulated arm has an optical arrangement for guiding a laser beam from the laser source along an optical path in the articulated arm to a target location. Within the optical path at least one crossing area (focus or focal point) of the laser beam is provided. The optical arrangement has at least one optical cell with an input window and an output window for passing the laser beam therethrough, wherein the crossing area is positioned within the optical cell. The optical cell has a gas fill with an energy threshold for ionization that is increased in comparison to that of ambient air.

13 Claims, 3 Drawing Sheets

*Fig. 4*
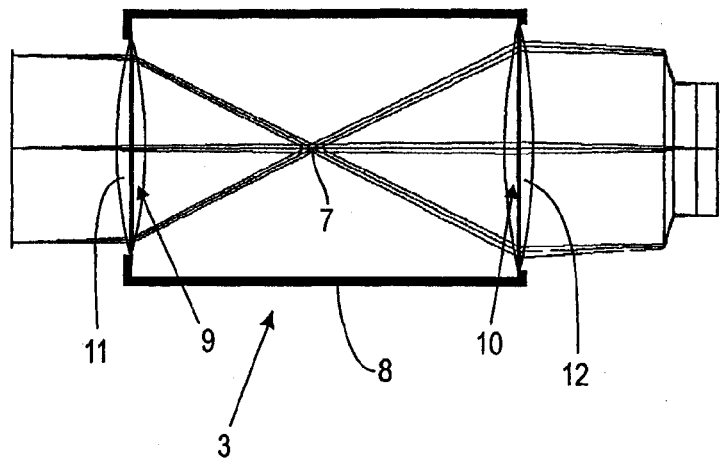
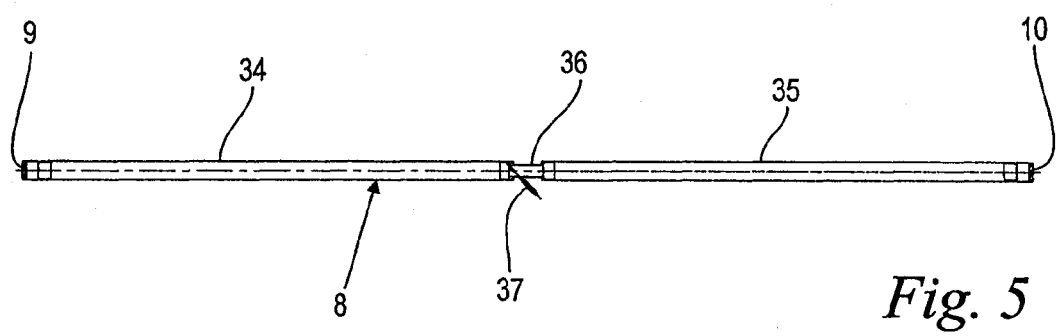
*Fig. 5*
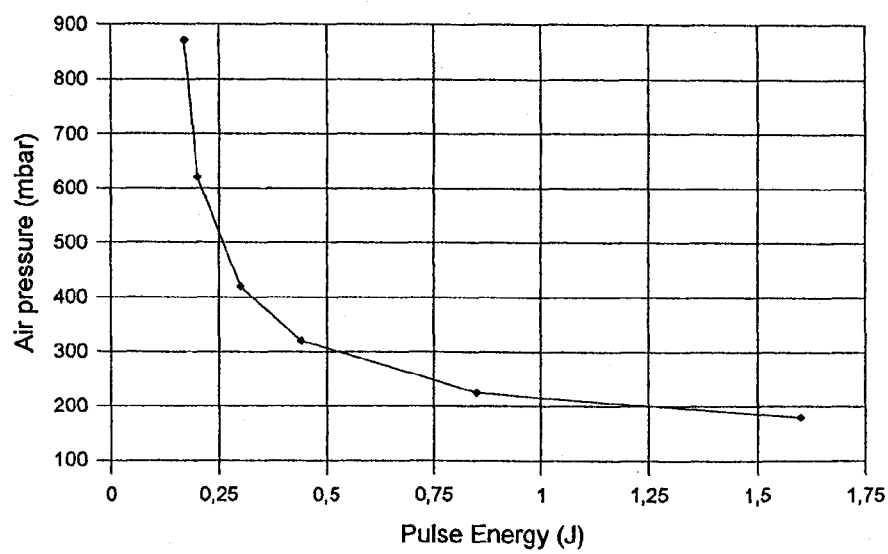
*Fig. 6*

LASER SYSTEM

BACKGROUND OF THE INVENTION

The invention relates to a laser system comprising a laser source and an articulated arm; wherein the articulated arm comprises an optical arrangement for guiding a laser beam from the laser source along an optical path within the articulated arm to a target location.

In technical and particularly in medical applications, the transmission of a laser beam from a laser source to a target location is realized either by a flexible light guide or along an optical path within an articulated arm. In the case of high-power lasers, the articulated arm is preferred for a couple of reasons: Fibers cannot withstand high optical power densities. When focusing a high power laser beam into a fiber, optical breakdown can occur before the beam reaches the fiber. In addition, unwanted nonlinear optical effects occur in the fibers.

In spite of this, disadvantageous effects that increase with increasing power density can be observed for laser transmission within an articulated arm. At an appropriate power level of the laser beam, the air within the optical path can become ionized; this causes a deterioration of the beam profile at the output. At very high power densities, the ionization of air causes plasma generation that, in turn, leads to optical breakdown of the laser transmission. As soon as the plasma generation has been excited by a first part of the laser pulse, the remaining part of the laser pulse is absorbed to a large extent.

In addition, the optical components of the articulated arm are exposed to conditions very close to damage threshold. In the case of novel Q-switched laser designs employing variable reflectivity technology in combination with the unstable resonator concept, the brightness of the output beam is even further increased, contributing particularly to thermal loading of the optical components.

The main characteristics of the beam emerging from such a laser are exceptional uniformity of the near-field beam profile and very low beam divergence so that, in this way, diffraction-limited conditions are approached. The uniform top hat profile is one of the most desirable profiles for many applications since it offers unique light-to-matter interaction conditions across the whole beam area. However, due to the high quality of the beam in terms of the M2 parameter, any change in laser resonator conditions, in particular variations related to the laser rod lensing due to different pumping conditions, result in accentuated variations of the beam farther away from the laser output. Not only the beam diameter is influenced in this way but the beam profile quality also deteriorates in comparison to highly desired near-field top hat conditions; this is usually unacceptable for laser applications.

To solve the problem to some extent, it is possible to trigger the laser flash-lamp at the highest repetition rate, and, by periodically activating the Q-switch cell, lower repetition rates can be obtained also. This kind of laser operation has many drawbacks. The laser pumping chamber operates at full pumping power most of the time, and this worsens problems concerning thermal load of the laser rod and related optical properties. Additionally, the lifetime of the flash-lamps is affected in this way and the overall electrical power consumption increases.

In order to solve the problems described above, an optical arrangement of the articulated arm may be considered that is based on the imaging of the plane of invariant beam profile onto the target plane. Such an optical arrangement is based on the fact that the beam change close to the laser output mirror is small and virtually does not change with the variation of the pumping conditions. This is particularly true in the case of unstable laser resonator concept with variable reflectivity output mirrors that can be optimized in such a way that beam profile propagation characteristics very close to the plane wave diffraction on a circular aperture are produced. The beam profile in the vicinity of the laser output is therefore close to top hat shape, and changes of beam diameter due to different lensing properties of the laser rod are small. Such an imaging of the plane of invariant beam profile onto the target plane is proposed in WO 01/78633 A2.

However, WO 01/78633 A2 does not teach in detail how imaging can be performed to achieve the desired goal. The optical arrangement of a high power laser system is usually designed in a way to maintain a reasonably large beam diameter throughout the beam path in the system. This approach reduces loading of the optical components and ionization of the air, but leads to a poor imaging quality.

The present invention has therefore the object to further develop a laser system of the aforementioned kind such that its optical transmission quality is improved, in particular at very high power density of the laser beam.

SUMMARY OF THE INVENTION

This object is solved by a laser system characterized in that the laser source has a plane, in which the beam profile does at least approximately not change with the variation of the pumping conditions, wherein the optical arrangement is designed for imaging the plane with the at least approximately invariable beam profile on the target location, that within the optical path at least one focal point of the laser beam is provided and in that the optical arrangement comprises at least one optical cell with an input window and an output window for passing the laser beam therethrough, wherein the focal point is positioned within the optical cell, and wherein the optical cell comprises a gas fill with an energy threshold for ionization that is increased in comparison to that of ambient air.

The present invention proposes that at least one crossing area (focus) of the laser beam is provided within the optical path, and that the optical arrangement comprises at least one optical cell with an input window and an output window, through which cell the laser beam is passed. The crossing area (focus) is positioned within the optical cell. The optical cell has a gas fill with an energy threshold for ionization or plasma generation which threshold is increased relative to that of ambient air.

The proposed solution means turning away from the conventional beam guiding concept, in which a beam diameter as large as possible is maintained along the entire optical path for reducing power density. The arrangement of a focus-like crossing area in the laser beam enables a configuration of the optical arrangement with exact imaging quality. Divergence phenomena or the like can be avoided almost completely, at least in approximation, at the target location; this improves the working results of the laser system.

In the crossing area the laser beam has a waist-like constriction with increased power density. Because this area is located within the optical cell, ionization or plasma generation is reliably prevented. A deterioration of the optical transmission or even an optical breakdown can be excluded even at high power density, because the increased energy threshold of the gas fill within the optical cell reliably prevents ionization or plasma generation.

The increased energy threshold of the gas fill can be achieved in different ways. For example, it can be expedient to select a suitable gas that is different from atmospheric air.

Alternatively, or in combination therewith, a reduction of the pressure of the gas fill in the optical cell relative to standard atmosphere can be advantageous. When employing vacuum, preferably air is used as an inexpensive gas fill that is available anywhere and is easy to handle technologically. The reduced pressure in the optical cell is in particular ≦600 mbar, expediently ≦400 mbar, and preferably ≦180 mbar; this raises effectively the ionization and plasma generation threshold. An even more reduced vacuum of the gas fill down to complete vacuum can be expedient also.

Depending on the type of application, the optical cell can be connected permanently to a suitable vacuum source. Advantageously, the optical cell is however gas-tightly sealed after adjusting the gas fill or the vacuum. After completion of manufacture, the sealed laser system is independent of gas sources and vacuum sources. The laser system has a simple configuration and is reliable in regard to handling.

It can be advantageous to configure the input window and/or the output window so as to be optically neutral, i.e., in the form of a plane-parallel glass plate, for example. Preferably, the input window and/or the output window are formed by a convergent lens.

In addition to providing the sealing function for the optical cell, windows that are configured as convergent lenses also provide an optical function. By means of the convergent lens at the input side, it is possible to generate within the optical cell the crossing point (focus, focal point) of the incoming, essentially parallel laser beam. By means of the convergent lens at the output side, the crossing beam section that widens in the output direction can be focused again such that the beam on the output side becomes parallel again, and that the cross-section of the output side remains completely on the optical path of the articulated arm. The number of optical component modules is therefore kept small.

Different locations are conceivable within the articulated arm system for arranging the optical cell. Preferably, the optical cell is arranged in an arm section of the articulated arm that can be moved in an articulated way. This provides for a sufficiently long interruption-free travel length in order to achieve an excellent imaging quality. Inasmuch as the articulated arm has at least two arm sections that can be moved in an articulated way, an optical cell is preferably arranged in each one of the two arm sections. In this connection, the transmission of the laser beam is realized, at least along a significant portion of the entire transmission path, within such an optical cell. The length of the two arm sections can be matched optimally to the requirements of the user. Impractical lengths of an individual arm section that would be required otherwise for an excellent imaging quality can be avoided in this way.

In the laser system according to the invention, the laser source is advantageously a pulsed high power laser with a pulse energy of at least 200 mJ, preferably at least 400 mJ, and in particular at least 800 mJ up to 1.6 J or greater. Preferably, the laser source is a Q-switched laser with technology of variable reflectivity and with unstable resonator concept. The laser source has a plane with at least approximately invariable beam profile wherein the optical arrangement is designed for imaging the plane with at least approximately invariable beam profile on the target location. In the configuration according to the invention, the divergence properties of the beam are no longer relevant for the beam diameter and the energy distribution within the beam diameter at the target location. The plane that is generated at the target location has in all operating states of the laser system an almost constant top hat-shaped beam profile.

The crossing area of the guided beam within the optical cell enables imaging of the desired uniform top hat profile on the target location without gas ionization or plasma generation within the optical path causing impairment of the intensity of the laser beam and its distribution across the beam cross-section.

BRIEF DESCRIPTION OF THE DRAWINGS

Embodiments of the invention will be explained in the following with the aid of the drawings. It is shown in:

FIG. 4 a variant of the arrangement according to FIG. 3 in which the input window and the output window of the optical cell are each formed as a convergent lens;

FIG. 5 in a side view an embodiment of an optical cell for generating the beam path according to FIG. 3 or FIG. 4, showing details of its constructive configuration;

FIG. 6 in a diagrammatic illustration the course of the air pressure required within the optical cell as a function of the pulse energy of the laser beam passing through the optical cell.

DESCRIPTION OF PREFERRED EMBODIMENTS

Figure 1:
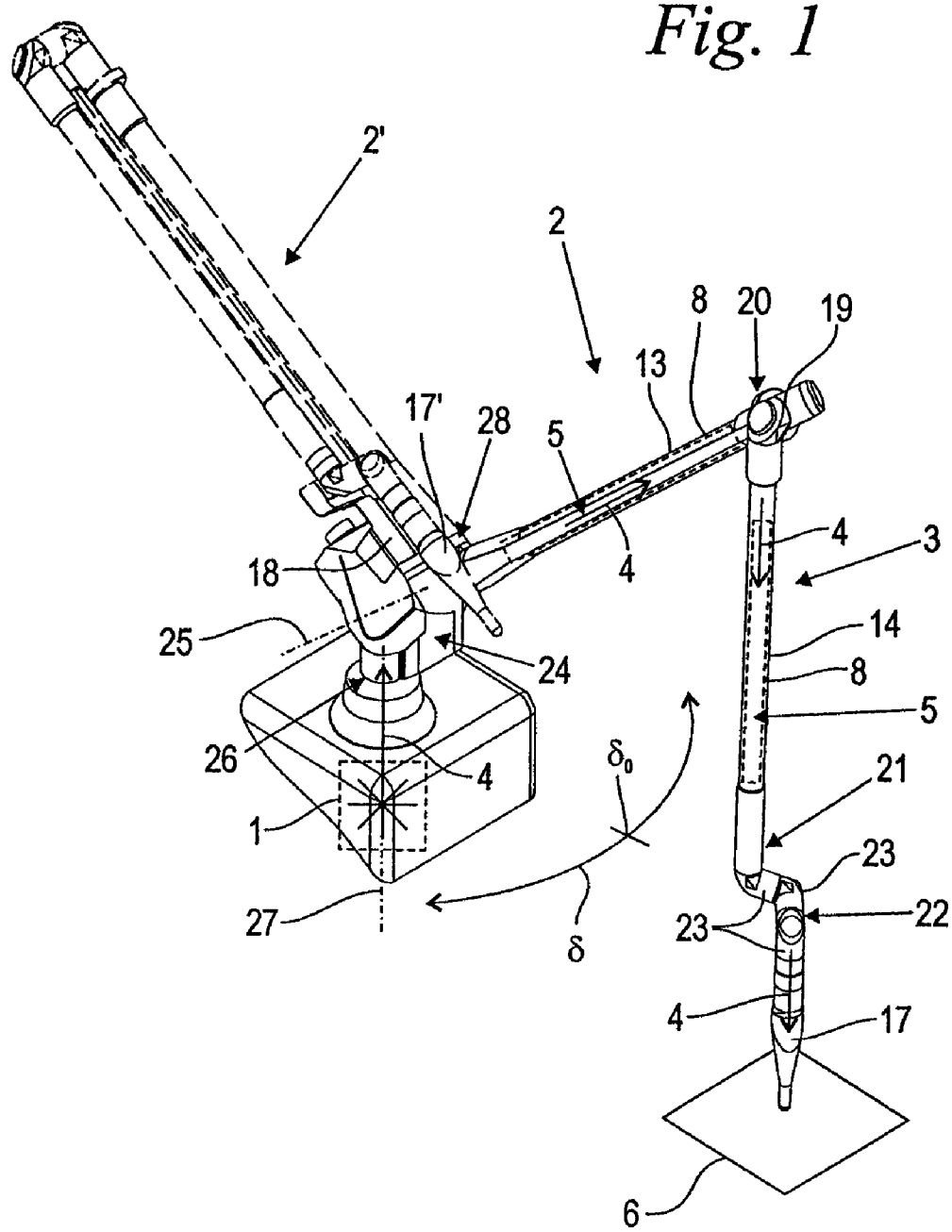
FIG. 1 in a perspective overview illustration a laser system in accordance with the present invention with a laser source and an articulated arm.

FIG. 1 shows in a perspective view a laser system embodied in accordance with the invention, comprising a laser source 1 and a manually guided articulated arm 2. The articulated arm 2 comprises a stationary support 24 that is pivotable by means of a pivot joint 26 about a vertical pivot axis 27; a first arm section 13 and a second arm section 14; an articulated arm section 22; and a hand piece 17. The first arm section 13 is supported by means of a pivot joint 28 with a horizontal pivot axis 25 on the stationary support 24. On the free end 20 of the first arm section 13 positioned opposite the pivot joint 28, an additional pivot joint 19 is provided with which the second arm section 14 is pivotably supported on the first arm section 13. In the area of the free end 21 of the second arm section 14, the hand piece 17 is arranged. Between the free end 21 of the second arm section 14 and the hand piece 17, the articulated arm section 22 is arranged that comprises at least two, in the illustrated embodiment three, angle pieces 23 to provide free movement of the hand piece 17.

The articulated arm, referenced by reference numeral 2 and shown in solid lines, is illustrated in an angular position that is provided for operation. By pivot movements of the pivot joints 28, 19, the articulated arm 2 can be pivoted back and forth between its operating position and a rest position in which the articulated arm is identified by reference numeral 2'. In its rest position, the articulated arm 2' rests with its hand piece 171 in the indicated support device 18. The articulated arm 2 can also be manually pivoted as a whole about the vertical pivot axis 27. In neutral angle, the articulated arm 2 can be moved from its illustrated operating position into the rest position indicated by 2' and placed onto the support device 18.

Figure 3:
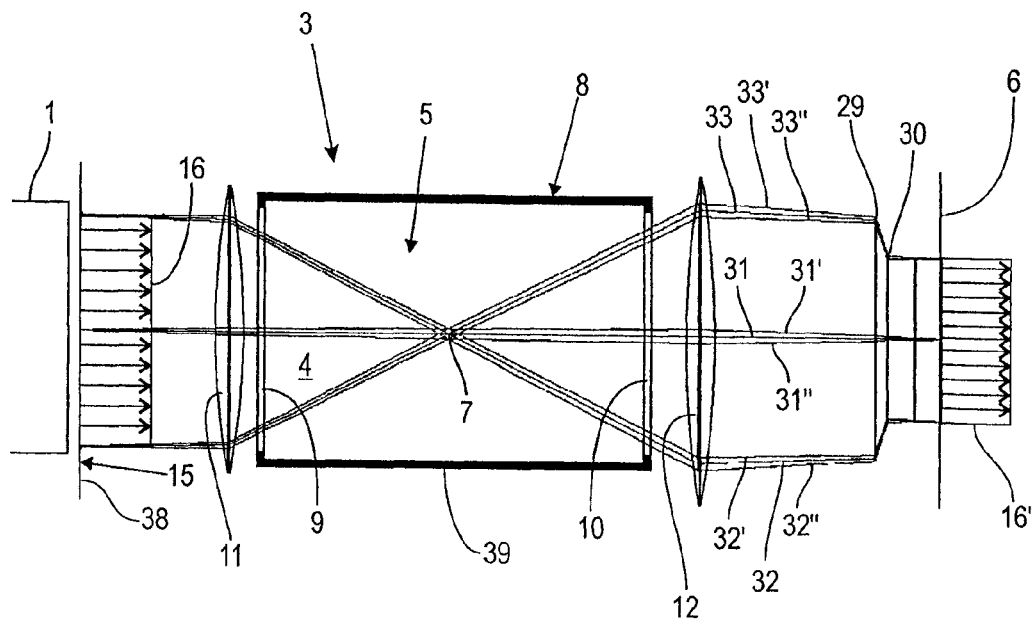
FIG. 3 a schematic illustration of the beam path in the optical arrangement of the laser system of FIG. 1 according to the present invention, wherein the optical arrangement has the effect of creating a crossing area of the laser beam within an optical cell.

In operation of the illustrated laser system, a laser source 1 generates a laser beam that is indicated by arrows 4 and is guided along an optical path 5 in the articulated arm 2 to the target location 6. For this purpose, the articulated arm 2 has an optical arrangement 3 that will be explained in detail in connection with FIGS. 3 and 4. It comprises two optical cells 8, illustrated in dashed lines; the arm section 13 and the arm section 14 each have one of the optical cells 8 arranged therein. Moreover, the optical arrangement 3 comprises angled mirrors, not illustrated, in the articulations and the angle members 23 of the articulated arm 2 as well as input window 9, output window 10, convergent lenses 11, 12, and lenses 29, 30 of the hand piece 17, as illustrated in FIGS. 3 and 4. By manually guiding the hand piece 17, the laser beam 4 is guided along the optical path 5 through the articulated arm 2 to the target location 6. In the illustrated embodiment, the laser source 1 is a pulsed high-power solid-state laser with a pulse energy of at least 200 mJ, preferably at least 400 mJ, and in particular at least 800 mJ. In this connection, the laser source 1 is configured as a Q-switched laser with technology of variable rate reflectivity and unstable resonator concept. The articulated arm 2 including its hand piece 17 is configured for a medical application. However, configurations and applications of the laser source 1 and of the articulated arm 2 different from medical applications can be expedient.

Figure 2:
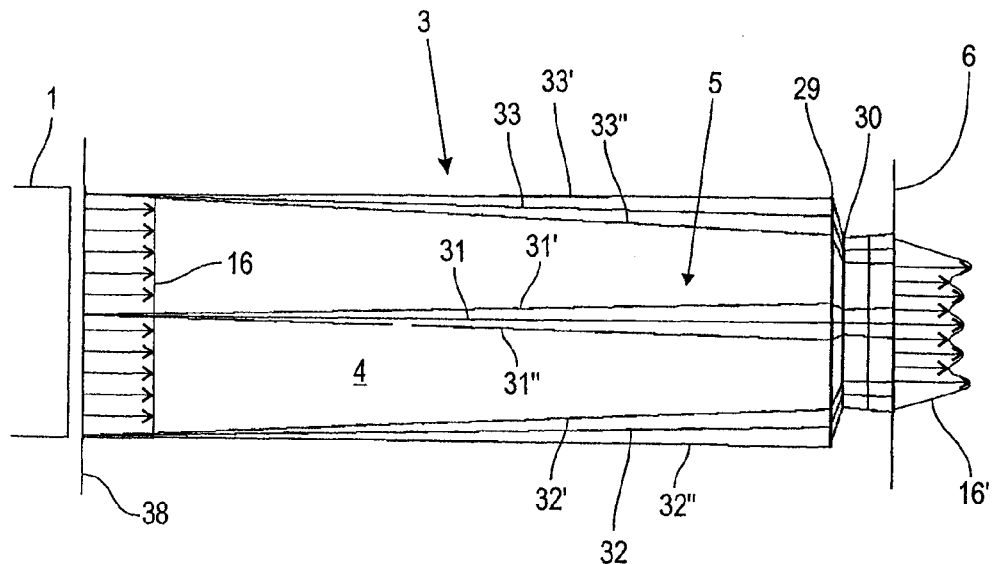
FIG. 2 a schematic illustration of the beam path according to the prior art with beam diameter variance and non-uniform beam profile at the target location.

FIG. 2 shows in a schematic illustration an optical arrangement 3 with optical path 5 in accordance with the prior art. The indicated laser source 1 generates at the output side of its correlated output mirror 38 a laser beam 4 with circular cross-section. The energy distribution in this circular cross-section is at least approximately constant so that a top hat-shaped beam profile 16 results. The bundle of approximately parallel rays of the laser beam 4 is focused in a hand piece, comparable to the hand piece 17 according to FIG. 1, by means of schematically illustrated lenses 29, 30 to the desired diameter and guided to the target location 6.

In order to explain the course of the beam, a central beam 31 as well as two marginal beams 32, 33 are shown in the illustration. Depending on the respective operating state of the laser source 1, its lensing properties are subject to change; this is illustrated by central rays 31', 31" as well as by marginal rays 32', 32", 33', 33". The beam diameter is limited with beams 32" and 33' in case of low laser rod lensing and with beams 32' and 33" in case of strong laser rod lensing. It can be seen that the diverging central rays 31', 31" and the marginal rays 32', 32", 33', 33" are guided by means of the optical arrangement 3 according to the prior art to the target location 6. With the given optical arrangement, the beam divergence influences the beam diameter at the target location 6. In addition, a non-constant beam profile 16' results at the target location 6, that is wave-shaped in cross-section and, in a projection onto the target location 6, is an arrangement of concentric rings with an energy distribution that is non-uniform in the radial direction.

FIG. 3 shows in a schematic illustration the optical arrangement 3 with the optical path 5 of the laser system according to the invention shown in FIG. 1, wherein, for clarity of illustration, only one of the two optical cells 8 is illustrated. It can be expedient to provide only a single optical cell 8 in one of the two arm sections 13, 14. Inasmuch as the articulated arm 2 according to FIG. 1 has more than two arm sections 13, 14, it can be advantageous to provide each of these arm sections with an optical cell 8, respectively. The laser source 1 comprises a laser rod with an output mirror 38; at its output side a beam profile 16 identical to the arrangement of FIG. 2 is generated. A plane 15 with an at least approximately invariable beam profile 16 is generated in which the diameter of the laser beam 4, despite changing pumping parameters, is essentially constant. In a given configuration of the laser source 1 with an unstable resonator and variable mirror technology, the plane 15 is approximately located at the location of the output mirror 38. In case of a stable resonator configuration, this plane 15 is located within the laser rod or in an opening delimiting the beam in the resonator.

The optical arrangement 3 arranged at the output side of the output mirror 38 comprises in addition to the lenses 29, 30 two schematically indicated convergent lenses 11, 12, between which the optical cell 8 with its input window 9 and output window 10 is arranged. Although a laser beam cannot exactly be represented with ray formalism, the beam path according to the invention is represented by rays 31, 32, 33 in order to better understand the optical scheme. The convergent lens 11 arranged upstream in the direction of the beam extension focuses the laser beam 4 in such a way, that the central ray 31 and the marginal rays 32, 33, including the diverging central rays 31', 31" and marginal rays 32', 33", 33', 33", cross at least approximately at a crossing point (focus). As a result of the divergence of the beam 4, a crossing area 7 rather than exactly a crossing point is generated. In the crossing area (focus) 7, the laser beam 4, in comparison to the beam profile 16 at the input side, has a characteristic beam waist with significantly reduced beam diameter in which a correspondingly increased power density is present.

At the output side of the crossing area 7, the cross-section of the laser beam 4 widens until it enters the downstream convergent lens 12. The convergent lens 12 arranged in the beam direction behind the crossing area 7 transmits the laser beam 4 at its output side so as to have a beam path that is at least approximately parallel or slightly convergent. This beam path is focused in the downstream lenses 29, 30 within the hand piece 17 (FIG. 1) to the desired beam diameter and guided to the target location 6. The lenses 29, 30 can have a variably adjustable spacing relative to one another so that a zoom function of the hand piece 17 (FIG. 1) results by means of which the beam diameter at the target location 6 can be adjusted.

The illustrated configuration of the optical arrangement 3 with the two convergent lenses 11, 12 and the intermediately positioned crossing area 7 has the effect, that the plane 15 with the at least approximately invariable beam profile 16 is imaged on the target location 6. In particular, the diverging central rays 31', 31" and marginal rays 32', 32", 33', 33", emerging from exemplary points of the plane 15, are guided at least approximately to the same corresponding point on the target location 6 as the correlated central ray 31 and the correlated marginal rays 32, 33. This optically sharp image of the plane 15 at the target location 6 has the effect that the input-side top hat beam profile 16 is imaged in such a way on the target location 6, that at this location a top hat-shaped beam profile 16' is produced, changed only with regard to its diameter and having at least approximately constant energy distribution. Varying lensing properties of the laser source 1 under operating conditions, as represented by marginal rays 32', 32", 33', 33", do not result in a change of beam diameter at the target location 6. The disadvantageous prior art effects (FIG. 2) of divergence and diameter variance of the laser beam 4 are thus eliminated.

The optical cell 8 arranged in the optical path 5 is essentially cylindrical and comprises a tubular circumferential wall 39. The input window 9 and the output window 10 are gastightly inserted into the two end faces of the circumferential wall 39. As a whole, the optical cell 8 or its interior are sealed to be gas-tight. The interior of the optical cell 8 has a gas fill with an energy threshold for ionization or plasma generation that is increased in comparison to that of ambient air. As a gas fill, a suitable gas that is different from ambient air can be selected. In the illustrated embodiment, the optical cell 8 contains air at reduced pressure relative to the standard atmosphere. The pressure of the gas fill is in particular ≦600 mbar, expediently ≦400 mbar, and preferably ≦200 mbar. Outside of the optical cell 8 ambient air is present. Relative to this ambient air, the reduced inner pressure of the gas fill within the optical cell 8 leads to the aforementioned increased energy threshold, as described infra in more detail in connection with FIG. 6.

Outside of the optical cell 8 the optical path 5 extends through ambient air in which also the convergent lenses 11, 12 are arranged. The comparatively great beam diameter does not have a sufficient power density in order to generate plasma in the ambient air. An optical impairment is therefore not to be expected. After the laser beam 4 has passed through the first convergent lens 11, the laser beam 4 passes through the input window 9 into the interior of the optical cell 8. The input window 9 that is transmissive for the laser beam 4 is formed in the illustrated embodiment as a plane-parallel glass plate, which optically does not affect the course of the laser beam 4 significantly. After passing the optical cell 8, the laser beam 4 passes through the output window 10 to leave the optical cell 8 and is then guided through the ambient air and reaches the downstream convergent lens 12. The output window 10 is also embodied as a plane-parallel glass plate without optically affecting the course of the beam. The crossing area 7 of laser beam 4 is positioned within the optical cell 8, i.e., in the area of the gas fill with increased energy threshold for ionization or plasma generation. By adjusting the reduced pressure in the aforementioned way, the energy threshold of the gas fill is increased such that the increased power density of the laser beam 4 in the crossing area 7 is not sufficient to effect ionization or even plasma generation of the gas fill. Despite the increased power density in the crossing area 7, the laser beam 4 can pass through the optical cell 8 without being affected.

FIG. 4 shows a variant of the arrangement according to FIG. 3 in which the input window 9 and the output window 10 of the optical cell 8 are each formed as a convergent lens 11 or convergent lens 12. In this connection, a separate arrangement of input window 9, output window 10, and convergent lenses 11, 12 in accordance with the illustration of FIG. 3 is not required. Instead, the function of generating the crossing area 7 is directly effected by the input window 9 and the output window 10. With regard to other features and reference numerals, the arrangement according to FIG. 4 is identical to that of FIG. 3.

For clarity of illustration, in FIGS. 3 and 4 details of the articulated arm 2 according to FIG. 1 are not shown. When looking at FIG. 1 as well as FIGS. 3 and 4, it is apparent that further components of the optical arrangement 3 such as angled mirrors or the like are arranged outside of the respective optical cell 8; they are thus positioned in an area of the laser beam 4 where its cross-section is not reduced by the convergent lenses 11, 12. In particular thermal loading of these components is thus minimal.

In FIG. 5 a side view of the optical cell 8 embodied in accordance with the invention is illustrated. It comprises two cylindrical tubes 34, 35 that are coaxially arranged to one another and connected by an intermediately positioned connecting piece 36. At the two free end faces of the tubes 34, 35, the input window 9 and the output window 10 are arranged. The connecting piece 36 has a connector 37 that is in communication with the interior of the optical cell 8. A vacuum pump can be connected by means of the connector 37 for reducing the interior pressure. After the desired reduced interior pressure has been adjusted, the connector 37 is sealed off so that the optical cell 8 and its interior as a whole is gastightly sealed. For certain applications, it can be expedient to not seal the connector 37 and to connect it instead permanently to a suitable vacuum source.

FIG. 6 shows a diagrammatic illustration of the air pressure to be adjusted within the optical cell 8 (FIGS. 3 to 5) as a function of the pulse energy of the laser source 1 (FIG. 1). The curve illustrated in the diagram of FIG. 6 illustrates the energy threshold of the exemplary embodiment of FIG. 5 at which, when surpassed, the air fill within the optical cell 8 has the tendency to generate plasma with optical breakdown in the crossing area 7. At the pulse energy of 200 mJ the air pressure within the optical cell 8 is therefore to be adjusted to ≦600 mbar. For a pulse energy of 400 mJ, the required air pressure is therefore ≦350 mbar; at a pulse energy of 800 mJ it should be ≦230 mbar. Even pulse energies of 1.6 Joule have been achieved without optical breakdown, having an air pressure of ≦180 mbar.

At a given pulse energy, it can be expedient to adjust the air pressure within the optical cell 8 to be significantly below the correlated threshold value for the air pressure in order to avoid disadvantageous effects by ionization even as no plasma is generated yet.

The application incorporates by reference the entire disclosure of European patent application 07 008 465 having a filing date of Apr. 26, 2007.

While specific embodiments of the invention have been shown and described in detail to illustrate the inventive principles, it will be understood that the invention may be embodied otherwise without departing from such principles.

What is claimed is:

1. A laser system comprising:
   a laser source emitting a laser beam;
   an articulated arm comprising an optical arrangement for guiding the laser beam from the laser source along an optical path within the articulated arm to a target location;
   wherein the articulated arm comprises at least one arm section moveable in an articulated way and further comprises a hand piece;
   wherein the laser source has a plane in which plane a beam profile of the laser beam at least approximately does not change when pumping conditions of the laser source are varied;
   wherein the optical arrangement is adapted to image the plane where said beam profile of the laser beam at least approximately does not change onto the target location;
   wherein within the optical path at least one crossing area of the laser beam is provided;
   wherein the optical arrangement comprises at least one optical cell arranged in said arm section, wherein said optical cell comprises an input window that is a convergent lens and an output window that is a convergent lens for passing the laser beam therethrough;
   wherein the at least one crossing area is positioned within said optical cell between the input window and the output window such that the input window focuses the laser beam on the crossing area and a cross-section of the laser beam widens from the crossing area toward the output window until the laser beam enters the output window and the output window transmits the laser beam to the hand piece; and
   wherein said optical cell comprises a gas fill with an energy threshold for ionization which energy threshold is increased in comparison to an energy threshold of ambient air.

2. The laser system according to claim 1, wherein the gas fill of the at least one optical cell has a pressure that is reduced relative to standard atmosphere, wherein said pressure is ≦600 mbar.

3. The laser system according to claim 2, wherein said pressure is ≦400 mbar.

4. The laser system according to claim 2, wherein said pressure is ≦180 mbar.

5. The laser system according to claim 2, wherein the gas fill is air.

6. The laser system according to claim 1, wherein the at least one optical cell sealed gas-tightly.

7. The laser system according to claim 1, wherein the articulated arm comprises at least two of said arm sections that each have one of said optical cell.

8. The laser system according to claim 1, wherein the laser source is a pulsed high-energy laser with a pulse energy of at least 200 mJ.

9. The laser system according to claim 8, wherein the pulse energy is at least 400 mJ.

10. The laser system according to claim 8, wherein the pulse energy is at least 800 mJ up to 1.6 J or greater.

11. The laser system according to claim 1, wherein the laser source is configured as a Q-switched laser with a variable reflectivity mirror and with an unstable resonator.

12. The laser system according to claim 1, wherein the output window transmits the laser beam at an output side of the output window so as to have a beam path that is at least approximately parallel or slightly convergent, and wherein the hand piece comprises at least one lens for focusing the laser beam of the output side of the output window to the target location.

13. The laser system according to claim 1, wherein said beam profile of the laser beam is an almost constant top hat-shaped beam profile.

* * * * *